United States Patent
Tamori et al.

(10) Patent No.: US 8,617,803 B2
(45) Date of Patent: Dec. 31, 2013

(54) NON-SPECIFIC ADSORPTION INHIBITOR, PROBE-BONDED PARTICLES, AND METHOD FOR PRODUCING THE SAME

(75) Inventors: Kouji Tamori, Tsuchiura (JP); Eiji Takamoto, Tsuchiura (JP)

(73) Assignee: JSR Corporation, Tokyo (JP)

( * ) Notice: Subject to any disclaimer, the term of this patent is extended or adjusted under 35 U.S.C. 154(b) by 1106 days.

(21) Appl. No.: 11/954,289

(22) Filed: Dec. 12, 2007

(65) Prior Publication Data

US 2008/0160167 A1 Jul. 3, 2008

(30) Foreign Application Priority Data

Dec. 14, 2006 (JP) ................................. 2006-336799
Sep. 12, 2007 (JP) ................................. 2007-236155

(51) Int. Cl.
*G01N 30/00* (2006.01)
*G01N 33/53* (2006.01)
*G01N 33/531* (2006.01)
*G01N 33/532* (2006.01)

(52) U.S. Cl.
USPC ................................. 435/4; 436/501; 436/518

(58) Field of Classification Search
USPC ....................... 435/4; 436/501, 518
See application file for complete search history.

(56) References Cited

U.S. PATENT DOCUMENTS

| | | | | |
|---|---|---|---|---|
| 5,596,027 A * | 1/1997 | Mead et al. | ..................... | 523/161 |
| 2006/0223126 A1 | 10/2006 | Tamori et al. | | |
| 2006/0240438 A1 * | 10/2006 | Nagasaki et al. | ................. | 435/6 |
| 2007/0099814 A1 | 5/2007 | Tamori et al. | | |
| 2007/0224424 A1 | 9/2007 | Tamori et al. | | |

FOREIGN PATENT DOCUMENTS

| | | | |
|---|---|---|---|
| EP | 1650565 | * | 7/2004 |
| EP | 1 650 565 A1 | | 4/2006 |
| JP | 11-287802 | | 10/1999 |
| JP | 11-352127 | | 12/1999 |
| JP | 3407397 | | 3/2003 |
| JP | 2006-226982 | | 8/2006 |
| WO | WO 2005/010529 A1 | | 2/2005 |

OTHER PUBLICATIONS

Derwent Publications, AN 2000-120425, XP-002475252, JP 11-352127, Dec. 24, 1999 (reference previously filed on May 19, 2008).
U.S. Appl. No. 12/529,824, filed Sep. 3, 2009, Katayose, et al.
U.S. Appl. No. 12/267,001, filed Nov. 7, 2008, Tamori, et al.
U.S. Appl. No. 13/025,273, filed Feb. 11, 2011, Takahashi, et al.
U.S. Appl. No. 11/914,986, filed Nov. 20, 2007, Takahashi, et al.
U.S. Appl. No. 11/772,616, filed Jul. 2, 2007, Tamori, et al.
U.S. Appl. No. 11/773,801, filed Jul. 5, 2007, Tamori, et al.
Derwent Publications, AN 2006-598639, XP-002475253, JP 2006-226982, Aug. 31, 2006 (reference previously filed on Dec. 12, 2007).
U.S. Appl. No. 13/121,124, filed Mar. 25, 2011, Tamori, et al.
U.S. Appl. No. 12/602,138, filed Nov. 27, 2009, Tamori, et al.
U.S. Appl. No. 11/961,562, filed Dec. 20, 2007, Tamori, et al.
U.S. Appl. No. 13/152,802, filed Jun. 3, 2011, Tamori, et al.
Notification of Reasons for Refusal issued Jul. 6, 2011 in Japanese Patent Application No. 2007-236155 (with English translation).
U.S. Appl. No. 13/763,236, filed Feb. 8, 2013, Takahashi, et al.
U.S. Appl. No. 13/218,494, filed Aug. 26, 2011, Tamori, et al.

* cited by examiner

*Primary Examiner* — Lorna M Douyon
*Assistant Examiner* — Amina Khan
(74) *Attorney, Agent, or Firm* — Oblon, Spivak, McClelland, Maier & Neustadt, L.L.P.

(57) ABSTRACT

A method for producing a non-specific adsorption inhibitor includes reacting (A) a tosylated compound of polyoxyethylene monomethyl ether with (B) a polyamine having either an amino group or imino group (—NH—), or both, in total of 3 to 12.

10 Claims, No Drawings

NON-SPECIFIC ADSORPTION INHIBITOR, PROBE-BONDED PARTICLES, AND METHOD FOR PRODUCING THE SAME

Japanese Patent Application No. 2006-336799, filed on Dec. 14, 2006, and Japanese Patent Application No. 2007-236155, filed on Sep. 12, 2007, are hereby incorporated by reference in their entirety.

BACKGROUND OF THE INVENTION

The present invention relates to a non-specific adsorption inhibitor which can be applied to the surface of particles for immunodiagnosis, for example, probe-bonded particles, and methods for producing the same.

In recent years, due to a demand for an increase in the inspection sensitivity for the early detection of diseases, an increase in sensitivity of a diagnostic agent has been an important subject. In order to increase the sensitivity of diagnostic agents using a solid phase such as magnetic particles, a method of using enzyme coloring as a detecting means is being replaced by a method of using fluorescence or chemiluminescence, both of which ensure higher sensitivity. Development of these detection techniques is said to have reached a level in which a one molecule-substance for inspection can be theoretically detected. In practice, however, the sensitivity is still insufficient. In diagnosis in which a specific substance is detected in the presence of biomolecules such as blood serum, coexisting biomolecules, secondary antibodies, luminescence substrates, and the like non-specifically adsorb on a solid phase. As a result, noise increases and interferes with promotion of the sensitivity. Therefore, in order to reduce the risk of a sensitivity reduction due to non-specific adsorption of substances other than the substances which can specifically bond to a solid phase surface used for an immunological reaction in an immunodiagnostic measurement, a biological material such as albumin, casein, or gelatin is usually used as a blocking agent (also referred to as a "non-specific adsorption inhibitor") to inhibit non-specific adsorption and reduce noise.

However, non-specific adsorption occurs in spite of the use of such a blocking agent. In addition, a biologically-derived blocking agent may have a risk of biological infection such as bovine spongiform encephalopathy (BSE). Therefore, development of a high performance blocking agent by chemosynthesis has been desired.

As a chemically-synthesized blocking agent, a vinyl monomer copolymer which has a polyoxyethylene side chain has been proposed (JP-A-11-287802). The proposed method of preparation of such a copolymer, however, can achieve only poor molecular weight reproducibility. The resulting copolymer product thus exhibits only poor blocking effect reproducibility. A polyoxyethylene having two amino groups in one molecular end used as a blocking agent has been proposed (Japanese Patent No. 3,407,397). This blocking agent, however, exhibits only inadequate mutual action with a solid phase. When added as a blocking agent, a major part remains in an aqueous phase, making the resulting product uneconomical. A block copolymer of a polyoxyethylene and pentaethylenehexamine has been proposed as a blocking agent (JP-A-2006-226982). Production and purification of such a block copolymer are difficult because a polyoxyethylene of which both ends are modified by pentaethylenehexamine is easily produced during synthesis of the copolymer. As a method for producing a block agent similar to the block copolymer of a polyoxyethylene and pentaethylenehexamine, a method of using a polyoxyethylene having an acetal end as an intermediate has been proposed (WO 2005/010529). Production and purification of such a block copolymer are difficult because the method produces a large amount of polyoxyethylene dimers.

SUMMARY

An object of the invention is to provide a chemically synthesized non-specific adsorption inhibitor which can be easily produced and exhibits a sufficient noise-reduction effect, prove-bonded particles, and methods for producing them.

In order to achieve the above object, the inventors have conducted extensive studies. As a result, the inventors have discovered a method for easily synthesizing a non-specific adsorption inhibitor and have further found that particles for immunodiagnosis treated with the non-specific adsorption inhibitor can exhibit a signal enhancing effect. These findings have led to the completion of the invention.

According to one aspect of the invention, there is provided a method for producing a non-specific adsorption inhibitor comprising reacting (A) a tosylated compound of polyoxyethylene monomethyl ether with (B) a polyamine having either an amino group or imino group (—NH—), or both, in total of 3 to 12.

In the above method for producing a non-specific adsorption inhibitor, (A) the tosylated compound of polyoxyethylene monomethyl ether may be a reaction product obtained by reacting a polyoxyethylene monomethyl ether with p-toluenesulfonyl chloride in the presence of an amine compound.

In the above method for producing a non-specific adsorption inhibitor, the amine compounds may be one or more compounds selected from a group consisting of trimethylamine hydrochloride, trimethylamine hydrobromide, trimethylamine hydrofluoride, trimethylamine sulfate, trimethylamine nitrate, trimethylamine phosphate, triethylamine, tripropylamine, and N,N,N',N'-tetramethylethylenediamine.

In the above method for producing a non-specific adsorption inhibitor, the amine compounds may be a mixture of trimethylamine hydrochloride and an amine other than triethylamine.

According to one aspect of the invention, there is provided a non-specific adsorption inhibitor comprising a compound shown by the following formula (1),

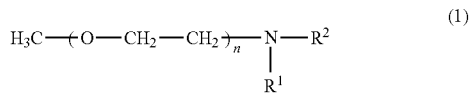

wherein n is a real number of from 4 to 2,000, $R^1$ and $R^2$ individually represent a hydrogen atom or a group possessing 1 to 11 amino group(s) or imino group(s), or both, provided that the total number of amino groups and imino groups contained in $R^1$ and $R^2$ is 2 to 11.

In the above non-specific adsorption inhibitor, the $R^1$ and $R^2$ in the formula (1) may respectively represent a group shown by the following formula (2a) and a group shown by the following formula (2b),

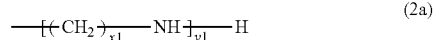

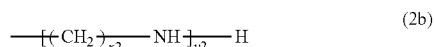

wherein x1 and x2 are respectively a real number of 1 to 4, and y1 and y2 are respectively a real number of 0 to 11, provided that y1+y2 is from 2 to 11.

According to one aspect of the invention, there is provided a method for producing probe-bonded particles comprising bonding a probe on each surface of particles and treating the probe-bonded particles with the above non-specific adsorption inhibitor.

In the above method for producing probe-bonded particles, the particles to be bonded with a probe may have at least one group selected from a group consisting of a carboxyl group, an active ester group, a tosyl group, and an epoxy group.

In the above method for producing probe-bonded particles, the particles may be magnetic particles.

According to one aspect of the invention, there is provided probe-bonded particles obtained by the above method for producing probe-bonded particles.

According to one aspect of the invention, there is provided probe-bonded particles wherein the above non-specific adsorption inhibitor is provided on surfaces of the probe-bonded particles.

The above non-specific adsorption inhibitor is easily produced, has no possibility of being biologically infected since it is a chemically synthesized product, and has a higher noise-reducing effect than general non-specific adsorption inhibitors.

In addition, the above non-specific adsorption inhibitor can exhibit a signal enhancing effect when applied to particles for immunodiagnosis (for example, magnetic particles).

DETAILED DESCRIPTION OF THE EMBODIMENT

A non-specific adsorption inhibitor, probe-bonded particles, and methods for producing these according to one embodiment of the invention are described below.

1. Non-Specific Adsorption Inhibitor and Method of Producing the Same

A non-specific adsorption inhibitor according to one embodiment of the invention is a reaction product of (A) a tosylated compound of polyoxyethylene monomethyl ether with (B) a polyamine having either an amino group or imino group (—NH—), or both, in total of 3 to 12. The non-specific adsorption inhibitor according to this embodiment is suitable, for example, as a signal enhancing agent of particles. The non-specific adsorption inhibitor according to this embodiment may be either the above reaction product itself or may optionally comprise a solvent.

Each of the components of the non-specific adsorption inhibitor according to this embodiment and a method for producing the same will be described below.

1.1. (A) Tosylated Product (A) The tosylated compound of polyoxyethylene monomethyl ether refers to alpha-methyl-omega-tosyl polyoxyethylene obtained by tosylating polyoxyethylene monomethyl ether. The term "tosylating" used herein refers to converting a hydroxyl group (—OH) into a p-toluenesulfonyloxy group (—OTs group).

Commercially available polyoxyethylene monomethyl ethers may be used in this embodiment. Polyoxyethylene monomethyl ethers having various molecular weights, for example, Uniox M series products (manufactured by NOF Corp.), MPG series products (manufactured by Nippon Nyukazai Co., Ltd.), and Leosolb PEM series products (manufactured by Lion Corp.) are industrially available.

The molecular weight of the polyoxyethylene monomethyl ether is preferably from 200 to 100,000, and still more preferably from 1,000 to 10,000. If the molecular weight is less than 200 or more than 100,000, the noise reduction effect and a signal enhancing effect may be insufficient.

A general method can be applied to the method for tosylating the polyoxyethylene monomethyl ether. For example, the hydrogen atom of the terminal hydroxyl group possessed by polyoxyethylene monomethyl ether is converted into a tosyl group by reacting the polyoxyethylene monomethyl ether with p-toluenesulfonate. Although not particularly limited, p-toluenesulfonyl chloride and the like can be given as examples of p-toluenesulfonate. The reaction is typically carried out by dissolving polyoxyethylene monomethyl ether in an organic solvent such as pyridine, dichloromethane, or acetonitrile, optionally adding an amine compound as a catalyst, adding p-toluenesulfonyl chloride in an amount of 1 to 5 mol per one mol of the polyoxyethylene monomethyl ether, and reacting the polyoxyethylene monomethyl ether with the p-toluenesulfonyl chloride at room temperature for 10 minutes to 24 hours. Alpha-methyl-omega-tosyl polyoxyethylene can be obtained by this reaction.

As the amine catalyst, trimethylamine hydrochloride, trimethylamine hydrobromide, trimethylamine hydrofluoride, trimethylamine sulfate, trimethylamine nitrate, trimethylamine phosphate, triethylamine, tripropylamine, N,N,N',N'-tetramethylethylenediamine, and the like can be used either individually or in combination. Combined use of trimethylamine hydrochloride and other amine compounds is particularly preferable in order to reduce the reaction time and to increase the tosylation rate. The amount of the amine catalyst used is preferably from 1.5 to 10 mol per one mol of polyoxyethylene monomethyl ether when an amine catalyst is used alone. In the case of using trimethylamine hydrochloride together with other amine compounds, 0.1 to 3 mol of trimethylamine hydrochloride and 1.5 to 10 mol of other amine compounds are preferably used per one mol of polyoxyethylene monomethyl ether. The alpha-methyl-omega-tosyl polyoxyethylene obtained by reaction may be purified by precipitating the product from diethyl ether, hexane, or the like. Such purification by precipitation can eliminate remaining p-toluenesulfonate and prevent a side reaction with a polyamine.

1.2. (B) Polyamine

The polyamine used in the non-specific adsorption inhibitor according to this embodiment is a polyamine (B) having either an amino group or imino group, or both, in total of 3 to 12.

If an amine compound having not more than two amino groups or not more than two imino groups, or an amine compound having one amino group and one imino group, such as a monoamine or diamine, is used, the resulting non-specific adsorption inhibitor exhibits insufficient mutual action with a solid phase. A major part of the non-specific adsorption inhibitor added remains in an aqueous phase, making the resulting product uneconomical. In addition, since the non-specific adsorption inhibitor is easily detached from the product during washing after the treatment, the noise reducing effect is insufficient. Moreover, the detached non-specific adsorption inhibitor may decrease signals by interfering with proteins and the like added to the sample to be analyzed.

On the other hand, if a polyamine having 13 or more amino groups and/or imino groups in total is used, the solid phase after treatment with the non-specific adsorption inhibitor becomes cationic due to amino groups, resulting in an increase in non-specificity and noise.

As specific examples of the polyamine (B) having 3 to 12 amino groups and/or imino groups in total, polymethyleneamines such as dimethylenetrimine, trimethylenetetramine, tetramethylenepentamine, pentamethylenehexamine, hexamethyleneheptamine, heptamethyleneoctamine, octamethylenenonamine, nonamethylenedecamine, decamethyleneundecamine, and undecamethylenedodecamine; polyethyleneamines such as diethylenetrimine, triethylenetetramine, tetraethylenepentamine, pentaethylenehexamine, hexaethyleneheptamine, heptaethyleneoactamine, octaethylenenonamine, nonaethylenedecamine, decaethyleneundecamine, and undecaethylenedodecamine; and propylenebutylene amines such as spermine and spermidine can be given. These polyamines may be used either alone or in combination of two or more. Taking the solubility in water and noise-reducing effect as a non-specific adsorption inhibitor into consideration, the polyamine (B) is preferably a polyethyleneamine, more preferably triethylenetetramine, tetraethylenepentamine, or pentaethylenehexamine, and still more preferably pentaethylenehexamine.

1.3. Method for Producing Non-Specific Adsorption Inhibitor

The reaction of (A) a tosylated compound of polyoxyethylene monomethyl ether with (B) a polyamine having either an amino group or imino group, or both, in total of 3 to 12 is typically carried out by dripping a solution of polyoxyethylene monomethyl ether (A) into a solution of a polyamine (B) in which 2 to 100 mol of the polyamine (B) per one mol of a tosylated compound of (A) is dissolved at a temperature range from room temperature to 60° C. over 1 to 24 hours. As a solvent, a non-protonic polar solvent such as acetonitrile, N,N-dimethylformamide, dimethylsulfoxide, and dimethylacetamide can be used. The non-specific adsorption inhibitor according to this embodiment is produced in this manner.

The produced non-specific adsorption inhibitor is preferably purified by precipitating from an organic solvent such as diethyl ether and isopropyl alcohol. As the organic solvent, a mixed solvent of a non-polar solvent and a polar solvent such as a mixed solvent of hexane and ethyl acetate is preferably used. As another purification method, a method of eliminating low molecular weight compounds by dissolving the produced non-specific adsorption inhibitor in water and subjecting the solution to a dialysis inner tube, a dialyzer, and an acylizer can be given. In this case, organic solvent may be removed by an evaporator before dissolving the non-specific adsorption inhibitor in water. Such purification can eliminate remaining polyamines, tosylated compounds, catalysts, and the like and can maintain a high noise-reducing effect.

1.4. Structure of Non-Specific Adsorption Inhibitor

A typical structure of the non-specific adsorption inhibitor according to this embodiment is an alpha-methyl-omega-poly-aminated polyoxyethylene.

In the non-specific adsorption inhibitor according to this embodiment, either a terminal primary amino group of a polyamine may be bonded to the terminal of a polyoxyethylene or a non-terminal secondary amino group of the polyamine may be bonded to the terminal of a polyoxyethylene.

In addition, two or more polyoxyethylene molecules may be bonded to one molecule of a polyamine. That is to say, both a terminal primary amino group of a polyamine and a non-terminal secondary amino group of the polyamine may be bonded to the terminal of a polyoxyethylene.

In view of the noise-reducing effect and signal-enhancing effect, the non-specific adsorption inhibitor according to this embodiment has preferably a structure in which one molecule of a polyamine is bonded to one molecule of a polyoxyethylene. It is possible to isolate the non-specific adsorption inhibitor having a structure in which one molecule of a polyamine is bonded to one molecule of a polyoxyethylene by column purification. The number of polyoxyethylene molecules bonded to one molecule of a polyamine can be confirmed by molecular weight measurement using liquid column chromatography.

In the non-specific adsorption inhibitor according to this embodiment, when a terminal primary or secondary amino group of a polyamine is bonded to a terminal of a polyoxyethylene, that non-specific adsorption inhibitor may contain a compound having a structure shown by the following formula (1),

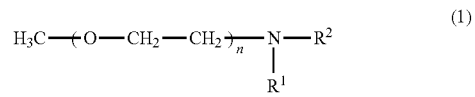

(1)

wherein n is a real number of 4 to 2,000, $R^1$ and $R^2$ individually represent a hydrogen atom or a group possessing 1 to 11 amino group(s) or imino group(s), or both, provided that the total number of amino groups and imino groups contained in $R^1$ and $R^2$ is 2 to 11.

In the formula (1), n is preferably 20 to 200.

In this instance, $R^1$ and $R^2$ in the formula (1) may respectively represent a group shown by the following formula (2a) and a group shown by the following formula (2b),

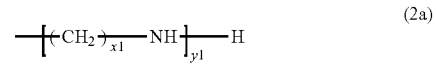

(2a)

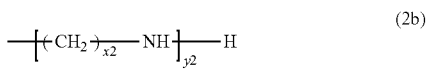

(2b)

wherein x1 and x2 are respectively a real number of 1 to 4, and y1 and y2 are respectively a real number of 0 to 11, provided that y1+y2 is 2 to 11.

In the above formula (2), x1 and x2 are preferably 2, and y1 and y2 are respectively a real number of 1 to 6, provided that y1+y2 is 2 to 11.

1.5. Application of Non-Specific Adsorption Inhibitor and Preparation of Probe-Bonded Particles If replaced with albumin, casein, gelatin, or the like which are used in common immunodiagnostic measurement, the non-specific adsorption inhibitor according to this embodiment can further suppress the non-specific adsorption and can inhibit noise.

In a plate method, for example, after bonding a probe such as an antibody to a plate, the non-specific adsorption inhibitor according to this embodiment can be added to treat the surface of the plate.

The non-specific adsorption inhibitor according to this embodiment can also be suitably used for preparing probe-bonded particles. The method for preparing probe-bonded particles according to this embodiment comprises bonding a probe on the surface of particles and treating the probe-bonded particles with the non-specific adsorption inhibitor according to this embodiment.

Treatment of the probe-bonded particles with the non-specific adsorption inhibitor according to this embodiment can be carried out by causing the non-specific adsorption inhibitor according to this embodiment to come in contact with the surface of the particles for a prescribed period of time. Non-specific adsorption on the surface of the particles can be inhibited and noise can be reduced by such a treatment. This treatment can be carried out by dispersing the particles in a solution of the non-specific adsorption inhibitor according to this embodiment.

In this instance, the particles to be bonded with a probe preferably have at least one group selected from the group consisting of a carboxyl group, an active ester group, a tosyl group, and an epoxy group. In addition, such particles are preferably magnetic particles.

More particularly, in order to obtain the probe-bonded particles in immunochromatography, for example, after boding a probe such as an antibody to colored particles, the non-specific adsorption inhibitor according to this embodiment is added to treat the surface of the colored particles. In order to obtain the probe-bonded particles in an assaying method such as EIA, CLIA, or CLEIA, for example, after boding a probe such as an antibody to the surface of the magnetic particles, the non-specific adsorption inhibitor according to this embodiment is added to treat the surface of the magnetic particles.

As described above, the non-specific adsorption can be inhibited and noise can be reduced by using the non-specific adsorption inhibitor according to this embodiment.

When the surface of particles (for example, magnetic particles) having a carboxyl group, an active ester group, a tosyl group, or an epoxy group at least on the surface is treated with the non-specific adsorption inhibitor according to this embodiment, the amino group in the non-specific adsorption inhibitor and the active group on the surface of the particles form a covalent bond, and orientation of an antibody used for immunodiagnosis is increased, whereby the effect of enhancing signals is exhibited. In addition, since detachment of the non-specific adsorption inhibitor can be inhibited, the probe-bonded particles can be an inspection reagent extremely stable to a buffering agent containing a surfactant and the like.

A carrier of the non-specific adsorption inhibitor according to this embodiment which can exhibit a particularly excellent effect is made up of particles (for example, magnetic particles) having a carboxyl group. A preferable treating method is a method of converting a carboxyl group on the particles into an active ester group using a water-soluble carbodiimide or the like, bonding an immunodiagnostic probe to the particles, and treating the resulting particles with the non-specific adsorption inhibitor according to this embodiment.

The probe-bonded particles according to this embodiment can be obtained by the above method for producing the probe-bonded particles. For example, the probe-bonded particles according to this embodiment may have the above-mentioned non-specific adsorption inhibitor on the surface.

2. EXAMPLES

The invention will now be described in more detail by way of examples, which should not be construed as limiting the invention.

2.1. Example 1

A separable flask equipped with a stirrer was charged with a solution of 10 g of a polyoxyethylene monomethyl ether having an average molecular weight of 4,000 ("Uniox M-4000" manufactured by NOF Corp.) dissolved in 100 g of pyridine. In another container, 2 g of p-toluenesulfonyl chloride was dissolved in 20 g of pyridine. This solution was added dropwide to the solution in the separable flask over one hour and reacted at room temperature for six hours. The reaction product was added dropwise to one liter of diethyl ether to precipitate and remove the remaining p-toluenesulfonic acid chloride. 8 g of a tosylated compound of the polyoxyethylene monomethyl ether (A-1) was thus obtained.

80 g of an aqueous solution containing 8 g of the tosylated compound (A-1) was added dropwise to 50 g of an aqueous solution containing 2 g of pentaethylenehexamine (B-1) while stirring at room temperature over two hours to react (A-1) with (B-1). The reaction product was added dropwise to one liter of diethyl ether to precipitate and remove the remaining pentaethylenehexamine (B-1). The resulting product was dried under vacuum to obtain 6 g of a non-specific adsorption inhibitor (C-1). Molecular weight distribution of the non-specific adsorption inhibitor (C-1) measured by liquid chromatography was found to have a broad peak with a main peak of molecular weight of 4,200. A small shoulder was observed on the high molecular weight side. Basicity measured by titration was 1.1 mmol/g.

Next, an aqueous solution of 1-ethyl-3-dimethylaminopropylcarbodiimide hydrochloride (manufactured by Dojindo Laboratories) was added to an aqueous dispersion of 1 mg of carboxyl group-containing magnetic particles ("MAG1101" manufactured by JSR Corporation) with a solid concentration of 1%. The mixture was stirred by rotation at room temperature for two hours to activate the carboxyl group. After removing a supernatant liquid by magnetic separation, 10 micrograms of an antibody to human alpha-fetoprotein (which is a tumor marker, hereinafter referred to as "AFP"), (the antibody was manufactured by COSMO BIO Co., Ltd. and is hereinafter referred to as "anti-AFP antibody") was added and reacted at room temperature for three hours. After the reaction, 125 microliters of the aqueous dispersion of the particles was added to a 0.4% aqueous solution of the non-specific adsorption inhibitor (C-1), and reacted at room temperature for 15 hours. After magnetic separation, the particles were repeatedly washed with a washing solution (25 mmol/liter Tris-HCl, 7.4 pH, containing 0.01% Tween 20), and diluted with the washing solution to a particle concentration of 0.5% to obtain protein-bonded particles (particles for immunoassay) with an anti-AFP antibody bonded as a primary probe. 10 microliters of a dispersion of the obtained probe-bonded particles (equivalent to 50 micrograms of particles) was added to a test tube and mixed with 50 microliters of a standard sample of an AFP antigen (manufactured by Nippon Biotest Laboratories Inc.) diluted with fetal calf serum (FCS) to a concentration of 100 ng/ml. The mixture was reacted at 37° C. for 10 minutes. After magnetically separating the particles and removing a supernatant liquid, 40 microliters of an anti-AFP antibody (a reagent attached to "Lumipulse AFP-N" manufactured by Fujirebio Inc.), labeled with an alkali phophataze (ALP) as a secondary antibody, was added, followed by a reaction at 37° C. for 10 minutes. Next, after magnetic separation and removal of a supernatant liquid, the resulting particles were washed three times with PBS and dispersed in 50 microliters of 0.01% Tween 20. The resulting dispersion was transferred to a new tube. After adding 100 microliters of an ALP substrate solution (Lumipulse substrate solution manufactured by Fujirebio Inc.), the mixture was reacted at 37° C. for 10 minutes to measure the amount of chemiluminescence.

A chemiluminescence luminometer ("Lumat LB9507" manufactured by Berthold Japan Co., Ltd.) was used for measuring the chemiluminescence. As a result, signal strength of the particles was found to be 123,563 RIU. Noise strength was measured in the same manner as above, except for using 50 microliters of FCS which does not contain the AFP antigen instead of 50 microliters of a standard sample of the AFP antigen diluted with fetal calf serum (FCS) to a concentration of 100 ng/ml. The noise strength was 67 RIU.

2.2. Comparative Example 1

A non-specific adsorption inhibitor of Comparative Example 1 was obtained in the same manner as in Example 1, except for using an ethylenediamine instead of the pentaethylenehexamine (B-1). Molecular weight distribution of the non-specific adsorption inhibitor of Comparative Example 1 measured by liquid chromatography was found to have a broad peak with a main peak of molecular weight of 4,000. Basicity measured by titration was 0.2 mmol/g. Signal strength was 109,104 RIU, and noise strength was 105 RIU.

2.3. Comparative Example 2

A non-specific adsorption inhibitor of Comparative Example 2 was obtained in the same manner as in Example 1, except for using a polyethyleneimine having a molecular weight of approximately 1,200 (average number of amino groups in a molecule: 28) instead of the pentaethylenehexamine (B-1). Molecular weight distribution of the non-specific adsorption inhibitor of Comparative Example 2 measured by liquid chromatography was found to have a broad peak of molecular weight of 11,000. Basicity measured by titration was 2.5 mmol/g. Signal strength was 65,503 RIU, and noise strength was 180 RIU.

2.4. Comparative Example 3

Signal and noise were measured in the same manner as in Example 1, except for using bovine serum albumin instead of the non-specific adsorption inhibitor (C-1). Signal strength was 92,762 RIU, and noise strength was 83 RIU.

2.5. Comparative Example 4

Signal and noise were measured in the same manner as in Example 1, except that the non-specific adsorption inhibitor (C-1) was not used. Signal strength was 94,673 RIU, and noise strength was 123 RIU.

It can be seen from the above results that, because the non-specific adsorption inhibitor (C-1) of Example 1 was a reaction product of (A) a tosylated compound of polyoxyethylene monomethyl ether with (B) a polyamine having either an amino group or imino group, or both, in total of 3 to 12, the probe-bonded particles of Example 1 in which the non-specific adsorption inhibitor (C-1) of Example 1 was used exhibited a sufficient noise-reduction effect as compared with the probe-bonded particles in which the bovine serum albumin was used as the non-specific adsorption inhibitor (Comparative Example 3) and the probe-bonded particles in which the non-specific adsorption inhibitor was not used (Comparative Example 4).

On the contrary, the probe-bonded particles in which the non-specific adsorption inhibitor of Comparative Example 1 was used exhibited an insufficient noise-reduction effect, because the non-specific adsorption inhibitor of Comparative Example 1 was a reaction product of (A) a tosylated compound of polyoxyethylene monomethyl ether with a polyamine having either an amino group or imino group, or both, in total of not more than two. The noise increased in the probe-bonded particles in which the non-specific adsorption inhibitor of Comparative Example 2 was used, because the non-specific adsorption inhibitor of Comparative Example 2 was a reaction product of (A) a tosylated compound of polyoxyethylene monomethyl ether with a polyamine having either an amino group or imino group, or both, in total of 13 or more.

2.6. Example 2

A separable flask equipped with a stirrer was charged with a solution of 100 g of polyoxyethylene monomethyl ether having an average molecular weight of 5,000 (manufactured by Fluka), 5 g of trimethylamine hydrochloride, 8 g of tripropylamine, and 8 g of p-toluenesulfonyl chloride dissolved in 300 g of acetonitrile. The solution was reacted at 30° C. for two hours while stirring to obtain a tosylated compound of the polyoxyethylene monomethyl ether (A-2).

Another separable flask equipped with a stirrer was charged with a solution of 47 g of pentaethylenehexamine (B-2) dissolved in 230 g of acetonitrile. The tosylated compound (A-2) was added dropwide to the solution while stirring and keeping the solution at 40° C. over one hour. The mixture was reacted by further stirring for nine hours. After the reaction, the solution was allowed to stand for 16 hours at room temperature and the precipitated byproduct was removed by decantation. The supernatant liquid obtained by decantation was concentrated using an evaporator and dissolved in 500 g of water. The solution was filtered and the filtrate was purified using a dialyzer to obtain a 2% solution of a non-specific adsorption inhibitor (C-2). Molecular weight distribution of the non-specific adsorption inhibitor (C-2) measured by liquid chromatography was found to have a peak with a main peak of molecular weight of 5,200. A small shoulder was observed on the high molecular weight side. Based on the ratio of the peak area of CH adjacent to imino groups to the peak area of the ether bond CH measured by proton NMR, the ratio of the polyoxyethylene monomethyl ether to the pentaethylenehexamine bonded was confirmed to be 1:1.

Next, an aqueous solution of 1-ethyl-3-dimethylaminopropylcarbodiimide hydrochloride (manufactured by Dojindo Laboratories) was added to an aqueous dispersion of 1 mg of carboxyl group-containing magnetic particles ("MAG2303" manufactured by JSR Corporation) with a solid concentration of 1%. The mixture was stirred by rotation at room temperature for two hours to activate the carboxyl group. After removing a supernatant liquid by magnetic separation, 10 micrograms of an antibody to human alpha-fetoprotein (which is a tumor marker, hereinafter referred to as "AFP"), (the antibody was manufactured by COSMO BIO Co., Ltd. and is hereinafter referred to as "anti-AFP antibody") was added and reacted at room temperature for three hours. After the reaction, 125 microliters of the aqueous dispersion of the particles was added to a 0.4% aqueous solution of the non-specific adsorption inhibitor (C-1), and reacted at room temperature for 15 hours. After magnetic separation, the particles were repeatedly washed with a washing solution (25 mmol/liter Tris-HCl, 7.4 pH, containing 0.01% Tween 20), and diluted with the washing solution to a particle concentration of 0.5% to obtain protein-bonded particles (particles for immunoassay) with an anti-AFP antibody bonded as a primary probe. 10 microliters of a dispersion of the obtained probe-bonded particles (equivalent to 50 micrograms of particles) was added to a test tube and mixed with 50 microliters of a standard sample of an AFP antigen (manufactured by Nippon Biotest Laboratories Inc.) diluted with fetal calf serum (FCS) to a concentration of 100 ng/ml. The mixture was reacted at 37° C. for 10 minutes. After magnetically separating the particles and removing a supernatant liquid, 40 microliters of an anti-AFP antibody (a reagent attached to "Lumipulse AFP-N" manufactured by Fujirebio Inc.), labeled with an alkali phophataze (ALP) as a secondary antibody, was added, followed by a reaction at 37° C. for 10 minutes. Next, after magnetic separation and removal of a supernatant liquid, the resulting particles were washed three times with PBS and dispersed in 50 microliters of 0.01% Tween 20. The resulting dispersion was transferred to a new tube. After adding 100 microliters of an ALP substrate solution (Lumipulse substrate solution manufactured by Fujirebio Inc.), the mixture was reacted at 37° C. for 10 minutes to measure the amount of chemiluminescence.

A chemiluminescence luminometer ("Lumat LB9507" manufactured by Berthold Japan, Co., Ltd.) was used for measuring the chemiluminescence. As a result, signal strength was found to be 182,983 RIU. Noise strength was measured in the same manner as above, except for using 50 microliters of FCS which does not contain the AFP antigen instead of 50 microliters of a standard sample of the AFP antigen diluted with fetal calf serum (FCS) to a concentration of 100 ng/ml. The noise strength was 72 RIU.

2.7. Comparative Example 5

A non-specific adsorption inhibitor of Comparative Example 5 was obtained in the same manner as in Example 2, except for using an ethylenediamine instead of the pentaethylenehexamine (B-2). Molecular weight distribution of the non-specific adsorption inhibitor of Comparative Example 5 measured by liquid chromatography was found to have a peak with a main peak of molecular weight of 5,000. Basicity measured by titration was N/A. Signal strength was 135,872 RIU, and noise strength was 107 RIU.

2.8. Comparative Example 6

A non-specific adsorption inhibitor of Comparative Example 6 was obtained in the same manner as in Example 2, except for using a polyethyleneimine having a molecular weight of approximately 1,200 (average number of amino groups in a molecule: 28) instead of the pentaethylenehexamine (B-2). Molecular weight distribution of the non-specific adsorption inhibitor of Comparative Example 6 measured by liquid chromatography was found to have a broad peak of molecular weight of 12,000. Signal strength was 72,377 RIU, and noise strength was 193 RIU.

2.9. Comparative Example 7

Signal and noise were measured in the same manner as in Example 2, except for using bovine serum albumin instead of the non-specific adsorption inhibitor (C-2). Signal strength was 129,246 RIU, and noise strength was 90 RIU.

2.10. Comparative Example 8

Signal and noise were measured in the same manner as in Example 2, except that the non-specific adsorption inhibitor (C-2) was not used. Signal strength was 127,195 RIU, and noise strength was 131 RIU.

It can be seen from the above results that, because the non-specific adsorption inhibitor (C-2) of Example 1 was a reaction product of (A) a tosylated compound of polyoxyethylene monomethyl ether with (B) a polyamine having either an amino group or imino group, or both, in total of 3 to 12, the probe-bonded particles of Example 2 in which the non-specific adsorption inhibitor (C-2) of Example 2 was used exhibited a sufficient noise-reduction effect as compared with the probe-bonded particles in which the bovine serum albumin was used as the non-specific adsorption inhibitor (Comparative Example 7) and the probe-bonded particles in which the non-specific adsorption inhibitor was not used (Comparative Example 8).

On the contrary, the probe-bonded particles in which the non-specific adsorption inhibitor of Comparative Example 5 was used exhibited an insufficient noise-reduction effect, because the non-specific adsorption inhibitor of Comparative Example 1 was a reaction product of (A) a tosylated compound of polyoxyethylene monomethyl ether with a polyamine having either an amino group or imino group, or both, in total of not more than two. The noise increased in the probe-bonded particles in which the non-specific adsorption inhibitor of Comparative Example 6 was used, because the non-specific adsorption inhibitor of Comparative Example 2 was a reaction product of (A) a tosylated compound of polyoxyethylene monomethyl ether with a polyamine having either an amino group or imino group, or both, in total of 13 or more.

Although the invention was described above in detail referring to this embodiment, those skilled in the art would readily appreciate that many modifications are possible in the embodiment without materially departing from the novel teachings and advantages of the invention. Accordingly, such modifications are intended to be included within the scope of the invention.

What is claimed is:

1. A method of inhibiting non-specific adsorption to an object, comprising:
   reacting a polyoxyethylene monomethyl ether with p-toluenesulfonyl chloride in the presence of two or more amine compounds, thereby producing (A) a tosylated compound of polyoxyethylene monomethyl ether, wherein said two or more amine compounds are selected from the group consisting of trimethylamine hydrochloride, trimethylamine hydrobromide, trimethylamine hydrofluoride, trimethylamine sulfate, trimethylamine nitrate, trimethylamine phosphate, triethylamine, tripropylamine, and N,N,N',N'-tetramethylethylenediamine;
   reacting (A) the tosylated compound of polyoxyethylene monomethyl ether with (B) a polyamine having either an amino group or an imino group, or both, in a total of 3 to 12, thereby producing a non-specific adsorption inhibitor; and
   treating a surface of an object with the non-specific adsorption inhibitor.

2. The method of inhibiting non-specific adsorption to an object as defined in claim 1, wherein the polyamine (B) has an amino group.

3. The method of inhibiting non-specific adsorption to an object as defined in claim 1, wherein the polyamine (B) has an imino group.

4. The method of inhibiting non-specific adsorption to an object as defined in claim 1, wherein the polyamine (B) has both an amino group and an imino group.

5. The method of inhibiting non-specific adsorption to an object as defined in claim 1, wherein the polyamine (B) is selected from the group consisting of dimethylenetrimine, trimethylenetetramine, tetramethylenepentamine, pentamethylenehexamine, hexamethyleneheptamine, heptamethyleneoctamine, octamethylenenonamine, nonamethylenedecamine, decamethyleneundecamine, undecamethylenedodecamine, diethylenetrimine, triethylenetetramine, tetraethylenepentamine, pentaethylenehexamine, hexaethyleneheptamine, heptaethyleneoactamine, octaethylenenonamine, nonaethylenedecamine, decaethyleneundecamine, undecaethylenedodecamine, spermine and spermidine.

6. The method of inhibiting non-specific adsorption to an object as defined in claim 1, wherein the polyamine (B) is selected from the group consisting of triethylenetetramine, tetraethylenepentamine, and pentaethylenehexamine.

7. The method of inhibiting non-specific adsorption to an object as defined in claim 1, wherein the polyamine (B) is pentaethylenehexamine.

8. The method of inhibiting non-specific adsorption to an object as defined in claim 1, wherein the object is probe-bonded particles.

9. The method of inhibiting non-specific adsorption to an object as defined in claim 1, wherein the object is a probe-bonded plate.

10. The method of inhibiting non-specific adsorption to an object as defined in claim 1, wherein said two or more amine compounds are trimethylamine hydrochloride and tripropylamine.

* * * * *